(12) United States Patent
Ellison

(10) Patent No.: US 7,816,118 B2
(45) Date of Patent: Oct. 19, 2010

(54) **METHODS FOR THE IN VITRO CULTURE OF *SPOROZOEA* SP. AND USES THEREOF**

(75) Inventor: Siobhan P. Ellison, Fairfield, FL (US)

(73) Assignees: Schering-Plough Corporation, Kenilworth, NJ (US); Pathogenes, Inc., Fairfield, FL (US)

( * ) Notice: Subject to any disclaimer, the term of this patent is extended or adjusted under 35 U.S.C. 154(b) by 483 days.

(21) Appl. No.: 11/754,498

(22) Filed: May 29, 2007

(65) Prior Publication Data

US 2007/0224223 A1 Sep. 27, 2007

Related U.S. Application Data

(62) Division of application No. 10/442,661, filed on May 20, 2003, now Pat. No. 7,250,286.

(60) Provisional application No. 60/382,428, filed on May 21, 2002.

(51) Int. Cl.
*C12P 1/02* (2006.01)
*C12N 1/14* (2006.01)

(52) U.S. Cl. .......... 435/258.4; 435/258.1; 435/171; 435/373; 424/93.5; 424/93.7

(58) Field of Classification Search .......... 424/93.1, 424/93.5, 93.7; 435/258.4, 258.1, 171, 325, 435/373
See application file for complete search history.

(56) References Cited

U.S. PATENT DOCUMENTS

| | | | |
|---|---|---|---|
| 3,147,186 A | 9/1964 | Edgar | |
| 4,438,097 A | 3/1984 | Shirley | |
| 4,544,548 A | 10/1985 | Davis et al. | |
| 4,650,676 A | 3/1987 | Schenkel et al. | |
| 4,808,404 A | 2/1989 | Bhogal | |
| 5,005,592 A | 4/1991 | Cartmell | |
| 5,068,104 A | 11/1991 | Bhogal et al. | |
| 5,311,841 A | 5/1994 | Thaxton | |
| 5,674,484 A | 10/1997 | Miller et al. | |
| 5,846,527 A | 12/1998 | Miller et al. | |
| 5,861,160 A | 1/1999 | Quick | |
| 6,306,385 B1 | 10/2001 | Lee | |
| 6,440,408 B2 | 8/2002 | Thoma et al. | |
| 6,500,438 B2 | 12/2002 | Evans et al. | |
| 6,808,714 B2 | 10/2004 | Dame et al. | |
| 7,169,398 B2 | 1/2007 | Bigbie et al. | |

FOREIGN PATENT DOCUMENTS

| | | |
|---|---|---|
| EP | 0 078 205 | 12/1985 |
| EP | 0231537 | 8/1987 |
| EP | 0 594 743 | 9/1999 |
| WO | WO 94/16725 | 8/1994 |
| WO | WO 96/40233 | 12/1996 |
| WO | WO 96/40234 | 12/1996 |
| WO | WO 99/47927 | 9/1999 |
| WO | WO 01/80885 | 11/2001 |

OTHER PUBLICATIONS

Speer, C.A. et al., Shedding of the Immunodominant P20 Surface Antigen of *Eimeria bovia* Sporozoites, Infection and Immunity, vol. 57, pp. 999-1001, 1989.
Speer, C.A., et al., Lymphokine-Induced Inhibition of Growth of *Eimeria bovis* . . . , Infection and Immunity, vol. 50, pp. 566-571, 1985.
Speer, C.A., et al., Comparative Development and Merozoite Production of Two Isolates . . . , J. Parasitol vol. 86, pp. 25-30, 2000.
Marsh, A.E., et al., In Vitro Cultivation and Experimental . . . , J. Parasitol, vol. 83, pp. 1189-1192, 1997.
Marsh, et al., Sequence Analysis and Polymerase Chain Reaction Amplification of Small Subunit Ribosomal DNA From Sarcocystis Neurons, AJVR, vol. 57, No. 7, Jul. 1996, pp. 975-981.
Stotish et al., Preparation and purification of merozoites of Eimeria tenella, The Journal of Parasitology, 61:700-703, 1975.
Xie et al., Electrophoretic and immunologic characterization of proteins of merozoites of Eimeria acervulina, E. maxima, E. necatrix, and E. tenella 1992.

*Primary Examiner*—Ruth A Davis
(74) *Attorney, Agent, or Firm*—Lucas & Mercanti, LLP

(57) ABSTRACT

The invention relates to a method of excysting and growing protozoal oocysts by in vitro tissue culture resulting in production of a continuous culture of merozoites. The invention also provides an economical and reliable supply of cultured *Eimeria* sp. for vaccine production, assays and research. Domesticated avians that have been vaccinated using the provied *Eimeria* sp. are also provided.

23 Claims, No Drawings

METHODS FOR THE IN VITRO CULTURE OF *SPOROZOEA* SP. AND USES THEREOF

CROSS-REFERENCE TO RELATED APPLICATIONS

This application is a divisional application of U.S. Ser. No. 10/442,661, filed on May 20, 2003, which in turn claims the benefit of provisional patent application U.S. Ser. No. 60/382,428, filed May 21, 2002, the contents of which are hereby incorporated by reference in their entireties.

FIELD OF THE INVENTION

The invention relates to culture systems and methods for the continuous culture of sporocyst-forming protozoa of the class *Sporozoea* and genera and species thereof. The invention also relates to merozoites and oocysts and related-*Sporazoea* life-stage cells produced by the inventive culture systems and methods, for use in vaccines, assays, and for other uses.

BACKGROUND OF THE INVENTION

The protozoa of the class *Sporozoea* include sporocyst-forming protozoa, many of which are etiologic in a myriad of diseases of animals and people around the world. Of particular commercial concern are the diseases caused by *Sporozoea* of the subclass *Coccidia*, order *Eucoccidiida* and suborder *Eimeriina*, as well as the sporocyst-forming protozoa of the genera *Cystoisospora, Eimeria, Isospora, Neospora, Sarcocystis, Toxoplasma, Tyzzeria* and *Wenyonella*.

In particular, coccidiosis is an enteric disease of animals, including domestic livestock e.g. poultry, caused by protozoan parasites of the subclass *Coccidia*, genus *Eimeria*. These are obligate intracellular protozoan parasites that replicate primarily in the intestinal epithelium. These parasites have a monoxenous life cycle and exhibit a high degree of host-species and tissue specificity. Overall, the combination of losses due to coccidiosis and the costs of prophylactic medication results in significant annual economic losses to the affected industries.

The economic effects of coccidiosis infections in domestic animals is especially severe in the poultry industry, where intensive housing of birds favors the spread of the disease. For fowl, e.g., poultry, and other domestic birds, *Coccidia* infection results in economic loss from stunting and skin discoloration. In addition, numerous *Eimeria* species can infect a single host via the oral route and/or by inhalation of the infectious particles from the environment. Once ingested, the parasite penetrates and damages the mucosal layer of the intestinal wall, causing acute morbidity, e.g, resulting in decreased growth and feed utilization in the infected avians.

Protozoa of the genera *Eimeria, Isospora, Cystoisospora*, or *Cryptosporidium* typically only require a single host to complete their life cycle. Under natural conditions, the life cycle begins with the ingestion of sporulated oocysts from the environment. The cell wall of the ingested sporulated oocyst is broken by mechanical disruption in the gizzard and/or digested by intestinal enzymes. Within the sporocysts are the sporozoites, which are the infective stage of the organism. The sporozoites invade the intestinal mucosa, or epithelial cells in other locations. The site of infection is characteristic of the species involved.

Within a host animal's cells, sporozoites develop into multinucleate meronts, also called schizonts. Each meront nucleus develops into an infective body called a merozoite, that enters new cells and repeats the process. After a variable number of asexual generations, merozoites develop into either microgametocytes or macrogametes. Microgametocytes develop into many microgametes which, in turn, fertilize the macrogametes. The resulting zygotes encyste by forming a tough outer coat, and are then called oocysts, which are shed unsporulated in the feces. Under proper environmental conditions, the oocysts sporulate and become infective. ingestion by susceptible animals then repeats the cycle.

Infection with *Coccidia* elicits a species-specific immunity. For example, there are seven known species of *Coccidia* which infect chickens, six of which are considered to be moderately to severely pathogenic.

Thus, in domestic avians, the introduction of another species of *Coccidia* or the introduction of new, previously unexposed birds may result in an outbreak of the disease. Oocysts are resistant to extremes in pH, detergents, proteolytic, glycolytic, and lipolytic enzymes, mechanical disruption (although they can be broken by laboratory methods) and chemicals such as sodium hypochlorite and potassium dichromate, and will survive for many weeks outside the host. For example, there are seven known species of *Coccidia* which infect chickens, six of which are considered to be moderately to severely pathogenic.

Numerous methods have been developed to immunize poultry against *Coccidia*. All commercially successful methods are based on the administration of live encysted protozoa, often of an attenuated strain. The most common route of inoculation is oral, although other routes have been used. Edgar, U.S. Pat. No. 3,147,186, teaches vaccination of chickens by oral administration of viable *E. tenella* sporulated oocysts. Davis et al., U.S. Pat. No. 4,544,548, teaches a method of vaccination by continuous administration of low numbers of sporulated oocysts, with or without simultaneous administration of anti-*Coccidial* drugs.

Attenuation can be achieved by serial passage in chickens. Selection of strains of *Coccidia* showing early formation of oocysts, and attenuation, has been described by U.S. Pat. No. 5,055,292, incorporated by reference herein its entirety.

Orally-administered attenuated strains of sporocysts have also been utilized to confer immunity against coccidiosis. [Shirley, U.S. Pat. No. 4,438,097; McDonald, U.S. Pat. No. 5,055,292; and Schmatz et al., PCT publication No. WO 94/16725]. An alternative to attenuation is disclosed in Jenkins et al., *Avian Dis.*, 37(1):74-82 (1993), which teaches the oral administration of sporozoites that have been treated with gamma radiation to prevent merogony.

Parenteral routes of vaccination have included subcutaneous or intraperitoneal injection of excysted sporozoites, Bhogal, U.S. Pat. No. 4,808,404; Bhogal et al., U.S. Pat. No. 5,068,104, and intra-ovo injection of either oocysts or sporocysts, Evans et al., PCT publication No. WO 96/40233; Watkins et al., Poul. Sci., 4(10): 1597-602 (1995). Thaxton, U.S. Pat. No. 5,311,841, teaches a method of vaccination against *Coccidia* by administration of oocysts or sporozoites to newly hatched chicks by yolk sac injection.

The need for viable protozoa for vaccination is a common factor in all of the current vaccination methods. Non-viable protozoa, or antigens from protozoa, have been unsuccessful in conferring the high level of immunity needed to protect against clinical infection.

Heretofore, viable, living protozoa, e.g. oocysts, have previously been harvested from living, intact infected avians. However, the use of live animals or, in some *Coccidia* species, chick eggs, to produce viable *Coccidia* cells for vaccine production is both costly and inefficient.

An economical and efficient alternative method for producing the required quantities of Coccidia for use in vaccine production, and other purposes, has long been sought. Propogation of Coccidia in vitro has been attempted, but with only limited success. Madin Darby Bovine Kidney (MDBK) cells have been reported to support *Eimeria* growth in vitro but the development is limited to one replication cycle of asexual development [D. M. Schmatz, *Adv, Cell Culture*, 5:241 (1987)]. *Eimeria* oocysts from *E. acervulina* [M. Nacri-Bontemps, *Ann. rech. Vet.*, 7:223 (1976)] and *E melea-grimitis* [Augustin et al, *J. Protozool.*, 25:82, (1978)] as well as *E bovis* [Speer et al, *Z. Parasitenkd*, (1973)], were obtained when initial host-derived merozoites have been used as the inoculum. However, as noted above, the requirement to use merizoites derived from infected animal tissues limits the usefulness of these approaches.

U.S. Pat. No. 5,846,527 describes an avian cell line derived from abnormal embryonic tissue that supports the growth of *E. tenella* and *E. necatrix*, but replication was sustained for only 72 hours. Another drawback is that an immortalized cell line derived from chickens provides a risk for transmitting tumorigenicity to chickens if used to make live vaccines.

Limited passage of merozoites has been known. For example, in U.S. Pat. No. 6,500,438, sporozoites were infected into primary chick kidney cells (PCI) that are grown in culture as cell aggregates, using a modification of the method described in D. J. Doran, *J. Parasit*. 57:891-900, (1971). However, once merozoites produced by this method are released, the culture is terminated. It is current dogma that *Eimeria* exhibits synchronized growth and therefore can not be induced to produce an immortal line of merozoites, ie., a line of merozoites that does not terminate, after a relatively short period of time, in the release of oocysts.

Therefore, there remains a longfelt and longstanding need for an economical and efficient method to obtain sufficient *Coccidia* cells for use in vaccine production and other endeavers. Growth of merozoites, in vitro, on immortalized mammalian cell would be desirable. However, as noted above, no in vitro culture system, providing suitable host cells, has previously been available that allows for indefinite propagation of the asexual phase of *Coccidia*, ie, the merozoites, with conversion to the infectious stage that can be induced only as required.

The citation of any reference herein should not be construed as an admission that such reference is available as "prior art" to the instant application

SUMMARY OF THE INVENTION

The present invention solves the above-identified problems as well as other problems by providing a method for continuous culture of obligate intracellular protozoa of class *Sporozoea* in the asexual phase of development. The inventive method includes the steps of: providing a cell culture system comprising immortalized host cells suitable for growing *Sporozoea* species, contacting the host cells with an infectious stage of the *Sporozoea* species under conditions effective for infection of the host cells, resulting in the growth of merozoites in the host cell; wherein the host cells are able to incorporate the protozoa by phagocytosis.

The inventive methods and culture system provided herein, allow for the production of heretofore unobtainable quantities of oocysts, merozoites and/or other life stages of protozoa of class *Sporozoea*. The availability of such quantities of these cells permits a wide variety of utilities, including providing viable *Sporozoea* cells for inclusion in live vaccines for animals, cells from which economical quantities of *Sporozoea* proteins and/or nucleic acids are readily obtained for any useful purpose, e.g., for diagnostics, protein-based vaccines, molecular biology and/or genetic studies of the organism, and the like.

The cell culture system includes a growth media suitable for maintaining the host cells and the *Sporozoea* species organism in culture. Any culture medium appropriate for the selected host cell line can be used.

In a preferred embodiment, the growth media includes a reducing agent, e.g., in a concentration effective to maintain the *Sporozoea* species organism in indefinite culture in a life cycle stage where reproduction is asexual. Any reducing agent compatible with the culture system can be employed, e.g., in a concentration that is functionally equivalent to about 0.01 to about 0.5 mM of β-mercaptoethanol.

Preferred host cells are immortalized cells retaining phagocytic activity that are derived from mammalian reticuloendothelial cells, e.g., an immortalized cell line derived from a monocyte cell line.

Preferred organisms to be cultured using the inventive methods and culture systems are protozoa of class *Sporozoea* that naturally infect only a single type of host cell, and that have not previously been successfully kept in indefinite cell culture on a commercial scale. These include, for example, *Coccidia* and/or e.g., *Eimeria, Isospora, Cystoisospora, Cryptosporidium* and combinations thereof, that infect avians. More preferred are members of the *Eimeria* species.

*Sporozoea* that naturally infect two types of host cell, e.g., *Neospora, Toxoplasma, Freankelia, Besnoitia, Hammondia*, and *Sarcocystis*, have generally been much more susceptible to long-term culture, and while they might grow in the cell culture systems of the present invention, these *Sporozoea*, are not preferred organisms for growth by these methods.

The invention also provides a protozoa of class produced by the inventive methods, as well as anti-protozoal vaccines comprising such protozoa. Methods of vaccinating avians against such protozoa of class *Sporozoea* are also provided.

Vaccine compositions comprising an organism produced by the inventive culture systems and methods are also provided that include, e.g., a pharmaceutically acceptable adjuvant or adjuvants, as well as art-known preservatives, colorants and the like. Optionally, a vaccine of the present invention can be admixed with drinking water, food grains or pellets for oral administration.

The invention further provides for avians that have been vaccinated using organisms produced by the inventive methods and cell culture systems.

The invention still further provides for a method of screening for agents which destroy or inhibit the growth of protozoa of class *Sporozoea* comprising culturing a *Sporozoea* species of interest as described supra, with and without contact with an agent to be screened, and detecting inhibition of growth or viability relative to growth in the absence of the agent of interest.

DETAILED DESCRIPTION OF THE INVENTION

Accordingly, the present invention provides culture systems that include host cells and methods for the in vitro continuous culture of sporocyst-forming protozoa of the class *Sporozoea*. Also provided are protozoal cells produced by a culture system of the present invention, e.g., *Sporozoea* merozoites and/or oocysts or other antigenic materials. Such materials can be used in the production of anti-*Sporozoea* vaccines for the vaccination of animals in need of protection from *Sporozoea* infections, e.g., humans, avians and domesticated animals, including domesticated birds.

Thus, the invention provides cell-culture systems and methods that will allow the asexual phase of *Sporozoea* cells to be maintained indefinitely, or for a sufficiently prolonged period of time, in vitro, to allow for the economical and efficient production of such cells.

The inventive culture systems and methods result in the production of viable and virulent, ie, infectious, culture populations of sporocyst-forming protozoa. These methods are generally applicable to any sporocyst-forming protozoa of the class *Sporozoea*, particularly of the subclass *Coccidia* and more particularly of the order Eucoccidiida and more particularly still of the suborder Eimeriina, and the sporocyst-forming protozoa of the genera *Cystoisospora, Eimeria, Isospora, Neospora, Sarcocystis, Toxoplasma, Tyzzeria* and *Wenyonella*.

The methods provided herein are contemplated to be useful for all *Sporozoea*, and particularly for *Coccidial* oocyst cultivation such as all avian infectious species of *Eimeria, Sarcocystis, Toxoplasma, Cryptosporidium, Isospora, Hammondia, Frenkelia,* and *Besnoitia*. The method of in vitro culturing replaces, and/or can supplement, the use of live animal growth and/or assays in the species that host the indicated parasites.

In an especially preferred embodiment, the invention is contemplated to be useful, e.g., for the in vitro culture of protozoa of the genera *Eimeria, Isospora, Cystoisospora,* or *Cryptosporidium* and others with similar single-host cell requirements. These protozoans have a specific receptor for their preferred host cell, and typically will not infect other cells, adding to the difficulty of culturing these cells. As noted supra, these protozoans typically require a single host to complete their life cycle.

In contrast, other genera of class *Sporozoea* require two hosts to complete their lifecycle. For example, *Neospora, Toxoplasma, Freankelia, Besnoitia, Hammondia,* and *Sarcocystis* require two hosts to complete their life cycle, and these have proved to be much less difficult to maintain in immortal cell culture, e.g., see, Dame et al., U.S. Patent Application No. 2002/0115828A1, the disclosure of which is incorporated in its entirety herein, describing the culture of *Sarcocystis neurona*.

It is protozoans that require a very specific single type of host, for which long term culture, in vitro, has heretofore proved to be an intractable problem, particularly in genera *Eimeria, Isospora, Cystoisospora,* or *Cryptosporidium* and other *Sporozoea* sp. requiring only a single host. The inventive methods solve this problem and provide methods and a cell culture system for the prolonged culture of these organisms.

Definitions

In order to better appreciate the scope and nature of the invention, the following terms are defined.

The term, "host cells" refers to immortalized cells of any mammalian species employed in the inventive culture system. Preferably, these are "phagocytic cells" that will incorporate protozoa by the process of phagocytosis, ie., the cells will engulf protozoa that it is desired to maintain in the culture system, so that the protozoa is incorporated into a phagosome. For example, the invention contemplates employing any phagocytic cell line that is adapted to in vitro culture and that will maintain the protozoa of interest. These include, e.g., cell lines derived from monocytes and their progeny, e.g., macrophages, as well as reticulum cells of the lymph nodes, spleen, and bone narrow, histiocytes, e.g., microglia of the central nervous system, alveolar macrophages, Kupffer cells of the liver and the like. The immortalized cells are optionally selected from those originating from bovine, porcine, canine, simian, feline, human, equine, ovine, murine, and/or lupine sources, to name but a few such animal sources. Immortalized cells are distinguished from so-called "primary" cell lines in that they do grow indefinitely in in vitro, whereas primary cell lines behave as they did in vivo, and will not replicate in vitro, indefinitely.

The term "culture" means the placement of oocysts or merozoites onto host cells and passage to new host cells, as required. Preferably, the number of protozoal cells in a typical culture system is greater than $10^6$, or in other embodiments, greater than $10^9$ cells, although these numbers may vary. The term "continuous culture", as used herein, unless otherwise indicated, means a cell culture that propagates indefinitely. Preferably, for the culture of *Eimeria*, a line that propagates and continues to grow in the asexual phase, in culture, for 18 days or longer, is a continuous culture. More preferably, a continuous culture continues to grow and remain in the asexual phase for as long as 150 days, or longer, and is readily preserved by chilling or freezing, followed by resumption of asexual growth after re-introduction into a suitable host cell.

The term "domesticated bird(s)", as used herein, unless otherwise indicated, includes chickens, turkeys, ducks, game birds (including, but not limited to, quail, pheasants, and geese) and ratites (including, but not limited to, ostrich).

The term "encysted" means the oocyst stage of the protozoan parasite.

The term "sporocyst" refers to the capsules than enclose the sporozoites in the oocyst. The time from ingestion of sporulated oocysts to emergence of oocysts in the feces is termed the prepatent time. This differs between the various *Eimeria* species.

The term "*Eimeria*", as used herein, unless otherwise indicated, means one or more species of the genus *Eimeria* that infect domesticated birds. *Eimeria* species include those that are found in chickens, and include, e.g., *E. tenella, E. acervulina, E. maxima, E. necatrix, E. mitis, E. praecox,* and *E. brunetti,* and also those that are found in turkeys, including *E. meleagrimitis, E. adenoeides, E. gallopavonis, E. dispersa, E. meleagridis, E. innocua,* and *E. subrotunda,* and also *Eimeria* species that infect other domesticated birds as defined above. The term "*Eimeria*" also includes all strains of the foregoing species of *Eimeria*, including, but not limited to, precocious strains, and attenuated strains, which includes strains that have been irradiated, or otherwise treated, so that they fail to complete development. The term *Eimeria* also includes any newly-discovered strains or species of *Eimeria* that infect domesticated birds as defined above.

The terms "oocysts", and "merozoites", as used herein, unless otherwise indicated, mean viable, ie, live, *Eimeria* oocysts, and merozoites, e.g., as obtained from the environment, animals, and the immortal cultures according to the invention.

As used herein, the terms "immunize" and "vaccinate" are synonymous and are used interchangeably. The term "effective immunizing dose", as used herein, unless otherwise indicated, means a number of oocysts or merozoites, or, when mixed, a number of oocysts and merozoites, sufficient to elicit an immune reaction in birds so vaccinated, e.g., a rise in anti-*Eimeria* sp. antibody titers and/or an activation of cell-mediated immunity. Preferably, the elicited immune reaction provides protective immunity, that limits or reduces clinical disease signs, weight loss, morbidity, and/or mortality in vaccinated birds that are challenged with a virulent dose of avian-specific *Eimeria* species.

Sources of *Sporazoea*

*Sporazoea* to be cultured by the inventive culture system are obtained from known samples, infected animal, e.g., blood, feces, tissues, or from contaminated environmental materials. If the population present in a sample, e.g., a sample of soil or a fecal sample, is primarily in the sporocyst stage, a sample of the population is simply cultured as described herein. If the population is primarily in the oocyst stage, the population can be induced to undergo sporulation by well-known methods for management of the environment, or a sample from the population can be induced to undergo sporulation using well-known laboratory methods. If the population or sample is primarily at the sporulated oocyst stage, sporocysts can be readily obtained by methods well known in the art, for example, mechanical disruption with glass beads.

Sources of Oocysts

Oocysts are obtainable from feces or tissue of infected animals; contaminated feed or water; soil; pen litter or bedding; or a variety of other sources. Methods for isolation of sporocysts are known. The exact procedures used to separate oocysts will vary with the material from which the oocysts are obtained and will be readily apparent to those skilled in the art.

The following summarizes one available approach to isolating organisms from raw environmental samples In brief, the initial step is separation of the oocysts from extraneous material. Soil or excreta is generally processed by forming a slurry with saturated saline solution and separating the sporocysts from the slurry. For example, the material to be processed is mixed with a minimum of 2 volumes (w/v) of saturated aqueous NaCl to form a slurry. If necessary, the slurry can be processed in a mixer or blender until a homogenous consistency is achieved. The slurry is centrifuged at about 800×g for 10 minutes at 4° C. The supernatant is collected by pouring through a double layer of 24×24 weave cheese cloth. Other methods to purify oocysts from samples that are commonly used include the Sheather sucrose flotation and Zinc-sulfate flotation, e.g., see L R Ash and T C Orihel, *Parasites: A Guide to Laboratory Procedures and Identification*, ASCP Press © 1991, incorporated by reference herein.

The filtered supernatant is diluted with two volumes of potable water and centrifuged at about 1600×g for 10 minutes at 4° C. The pelleted oocysts are washed with water and pelleted by centrifugation as described an additional three times. The oocysts are then washed three times in 2.5% potassium dichromate using the same procedure used for the water washes. After the final wash, the oocysts can be stored in 2.5% potassium dichromate at 4° C. or transferred to a container for sporulation.

Alternatively, sequential filtration can be used to isolate oocysts based on size. If filtration is used, the oocysts are washed with water and 2.5% potassium dichromate as previously described.

Sporulation

It is possible to induce sporulation in oocysts by art-known methods. For example, sporulation can be accomplished by placing oocysts in a solution of 2.5% potassium dichromate in a container and placing a cotton or foam rubber plug in the opening. The container is agitated on an orbital shaker at 250 rpm and 28-30° C. for 48-72 hours. Alternatively, the solution containing the oocysts can be constantly agitated while air is bubbled through the solution at about 25 to 75 cubic feet per hour. During the sporulation process, samples are withdrawn at regular intervals and tested for sporulation by microscopic examination of the oocysts to determine if they contain sporocysts.

Alternatively, if the sample is to be obtained from the environment, for example, floor litter, the litter can be managed to provide the proper conditions of moisture and temperature to cause natural sporulation.

Following sporulation, sporulated oocysts are collected by filtration, centrifugation or other acceptable concentration procedures known to those skilled in the art. For example, sporulated oocysts can be concentrated by centrifugation at about 1600×g for 10 minutes at 4° C. and the supernatant discarded. After concentration, sporulated oocysts may be disinfected by suspension in 5.25% sodium hypochlorite for 10 minutes at 4° C. Following disinfection, the sporulated oocysts are removed from the sodium hypochlorite by centrifugation at 1600×g for 10 minutes at 4° C. or other acceptable means. The sporulated oocysts are then washed four to six times with sterile water. After washing, the sporulated oocysts can be stored in 2.5% potassium dichromate, phosphate buffered saline (PBS) containing 30 µg/ml gentamicin or other acceptable disinfectants.

The sporulated oocysts can be disrupted to obtain sporocysts free of the outer coat, by art-known methods, e.g., mechanical disruption and/or proteolytic digestion of the outer coat. One convenient method is as follows. In brief, sporulated oocysts, e.g., optionally those separated from environmental material (soil or feces) as described supra, are diluted to a concentration of about $2 \times 10^6$/ml in PBS. One ml aliquots of this PBS are added to 1.5 ml microfuge tubes containing 125 µl of 0.5 mm glass beads. The tubes are then vortexed at high speed for five minutes, and then chilled on ice. Following vortexing, the supernatant is removed and saved. The glass heads are then washed with PBS and the supernatant saved and combined with the supernatant obtained after vortexing. The supernatant is then centrifuged at about 900×g for about two to three minutes and the supernatant discarded. The pellet with the sporocysts is resuspended in 0.2 ml of PBS. The concentration of sporocysts per ml is then determined by using a hemacytometer or other method of determining cell number.

Culturing *Sporazoea* on Host Cell Line In Vitro

For convenience of description, the culture system is described in terms of a batch culture system. The artisan will appreciate that the culture system and the associated method are readily adapted to other art-known methods for growing cells in culture, including batch-fed and continuous culture systems. Detailed descriptions of a number of art-known methods for growing animal cells in vitro are described, for example, by R. Ian Freshney, *Culture of Animal Cells*, Fourth Edition, John Wiley & Sons, Inc. © 2000, incorporated by reference herein in its entirety.

For the inventive culture system, the starting population can be either a naturally occurring population or one maintained in the laboratory. If the population contains primarily oocysts or sporulated oocysts, it is not necessary to excyst the parasites according to this invention if a phagocytic cell line is used as the host cells, that accomplishes release in phagolysosomes.

The sporocysts in the sample are cultured with host cells for a period of time to allow sporulation/excystation and growth of merozoites, amplified within each host cell. This time period will vary for different host cells and species of merozuites, but is typically about 72 hours for *Eimeria* sp.

Maintenance media, e.g., a culture media as defined herein, is not replaced but rather, fresh media is added every three days. The cultured merozoites are allowed to mature and produce oocysts or sporocysts. The incubation time typically ranges from about 4 to about 30 days. For example, a typical time to produce merozoites in culture is about 10 days, and a typical time to produce oocysts is 18 days.

In particular, if the culture is not divided, and is allowed to increase in density, at about 18 days oocysts or sporocysts are released into the culture medium. Otherwise, with appropriate splitting of the culture, ie., periodic reduction in the cell density, the culture continues to produce merozoites.

The sporocysts are harvested from the maintenance media by centrifugation, and preserved either by refrigeration, cryopreservation, or freeze drying. Merozoites are harvested by removing an aliquot of cultured cells, generally limited to about $\frac{1}{20}$ of the culture volume of infected host cells. The aliquot is then inserted onto a sub-confluent layer of freshly-trypsinized host cells. In laboratory scale production, the optimum frequency of transfer of the merozoites has typically been about every 10 days, although this will vary somewhat with particular host cell lines, species of *Sporozoea*, and/or as the culture system is scaled. If the merozoites are being passed between two cell lines in order to achieve increased virulence, or virulence to a new host strain, the optimum time of transfer is preferably, but not limited to, 4 days. Infection of host cells is then determined using any means suitable for staining and detecting the stained protozoa (e.g., Giemsa stain). By correlation, the viability of the protozoa in the original population can be estimated based on the extent of staining of the protozoa in the sample. Potency testing can be related to viability by live bird assay. The live bird assay can validate the in vitro potency test to prepare a vaccine.

In one preferred embodiment, the invention provides a culture system capable of supporting the growth and the excystation, in continuous culture of *Eimeria* sp. The culture system maintains the merozoite population in its asexually-dividing form for as long as required, and when required, the culture system can induce the merozioites to encyst, ie, to terminate the merozoites as oocysts for vaccines, or other uses. The host cells of the inventive culture system are any suitable immortalized mammalian cell line that can be economically adapted to the inventive methods.

In another preferred embodiment, the host cells are selected from immortalized phagocytic cells that will support the excystation and growth of *Eimeria* sp., and that are able to thrive in continuous culture, e.g., immortalized cells that originated from, e.g., mammalian reticuloendothelial cells. These include, for example, monocytes and their progeny, e.g., macrophages, as well as reticulum cells of the lymph nodes, spleen, and bone narrow, histiocytes, microglia of the central nervous system, alveolar macrophages, Kupffer cells of the liver, and the like. The immortalized cells are optionally selected from those originating from bovine, porcine, canine (e.g., ATCC CRL 10389), simian, feline, human (e.g., ATCC TIB202), equine, ovine, murine (e.g., ATCC TIB 61), and/or lupine sources, to name but a few such sources.

Without meaning to be bound by any theory or hypothesis as to how the invention might operate, it is believed that phagocytic cells are optimal for culturing *Sporozoea* organisms, in part, due to their ability to take up the parasite cells into intracellular phagosomes.

In yet another preferred embodiment, the invention also provides a screening system for identifying suitable host cells for use in the culture system. In brief, a suitable host cell is identified by employing the inventive culture system, as exemplified hereinbelow, and substituting a candidate host cell for the bovine monocyte cell line of those examples, and determining the longevity and growth of merozoites in the substituted culture system relative to that achieved with the bovine monocyte cells, all other parameters being the same or similar. Suitable host cells, e.g., phagocytic cells, will provide longevity and growth for *Sporozoaea* organisms that is useful for long term culture of such organisms in the asexual reproductive state, e.g., at least as successfully as do the exemplified bovine monocyte cells for *Eimeria* sp. and related organisms.

In a further preferred embodiment, the host cells are cultured in a medium suitable for long term culture of the selected host cells, and also including a reducing agent, e.g., a reducing agent in a concentration having reducing activity that is the functional equivalent of about 0.01 to about 0.5 mM beta-mercaptoethanol. A suitable reducing agent is any reducing agent that enhances the longevity of *Sporozoaea* organisms in long term culture, e.g., including *Eimeria* sp.

In one particular optional embodiment, dithiothreatol ("DTT") is excluded from preferred reducing agents according to the invention.

In a still further preferred embodiment, the invention provides a screening system for identifying suitable reducing agents for use in the culture system. In brief, a suitable reducing agent is identified by employing the inventive culture system, as exemplified hereinbelow, and substituting a candidate reducing agent for the β-mercaptoethanol of those examples, and determining the longevity and growth of merozoites in the substituted culture system relative to that achieved with and without β-mercaptoethanol, for example, at analogous levels of reducing activity, relative to those successfully employed for β-mercaptoethanol. Suitable reducing agents will provide longevity and growth for *Sporozoaea* organisms that is useful for long term culture of such organisms in the asexual reproductive state, e.g., at least as successfully as does β-mercaptoethanol for *Eimeria* sp. and related organisms.

Simply by way of example, preferred reducing agents are agents that reduce disulfide bonds, and include β-mercaptoethanol, mercaptoethylamine, 2,3-dimercaptosuccinic acid, penicillamine, β-lactams, N-acetylcysteine, ascorbate, and their equivalents and/or combinations thereof The artisan will likewise be able to optimize the concentration of a suitable reducing agent by routinely employing the exemplified cell culture system, while varying concentrations of a selected reducing agent, and holding other parameters constant, in order to determine optimal culture productivity and longevity. For example, for a reducing agent of interest, concentrations of increasing levels can be tested to determine the level at which the benefits no longer improve with increased concentration or the levels at which any negative effects of the reducing agent outweigh the benefits to culture productivity and longevity.

Most preferably, the reducing agent is β-mercaptoethanol, in a concentration in the cell culture medium ranging from about 0.01 m/M to about 0.5 mM, or higher, and more preferably, in a concentration of about 0.055 mM. Without meaning to be bound by any theory or hypothesis as to how the invention might operate, it is believed that, at the concentrations employed, generally less than 1 mM, and preferably less than 0.1 mM, the reducing agents selectively interfere with host cell and/or parasite signals relating to parasite sexual differentiation and/or a release signal event.

Without meaning to be bound by any theory or hypothesis as to how the invention might operate, it is hypothesized that, in one alternative embodiment, a reducing agent inhibits a phagocytic host cell from digesting or killing protozoa incorporated into host cell phagosomes, thus effectively contributing to the viability of the protozoa parasite in culture within a line of phagocytic host cells.

In a more preferred embodiment, the host cell culture system employs both a phagocytic immortalized cell line and a culture medium that includes a suitable reducing agent, e.g., β-mercaptoethanol or its functional equivalent, e.g., in the above-stated concentration ranges, e.g., for the continuous culture of *Eimeria* sp. organisms.

In a most preferred embodiment, the host cells are bovine monocyte cells (sometimes referred to as BM617) from Speer et al, 1985, *Infection and Immunity* 50:566-571, incorporated by reference in its entirety herein (Dr. Speer,: College of Veterinary Medicine, College Station, Tex.) Bovine monocytes that are derived from ATCC CRL 6017 and ATCC CRL 6057 are also exemplified.

The inventive culture system employs culture media, densities, optional growth substrates or surfaces, temperatures and atmosphere as appropriate to the selected host cells. Optionally, the host cells grow in suspension with flask stirring or rotation. Alternatively, e.g., for host cells requiring a solid substrate, the cells grow on flask surfaces, on slides immersed in the growth medium, in Petri dishes, and/or on the surface of micro-beads, optionally magnetic, suspended in the growth medium, or on any other art-known cellular growth support appropriate to the selected host cells.

For example, when employing the bovine monocyte cells exemplified herein and noted supra, the cells are preferably seeded in an about 150 cm$^2$ tissue culture flask at a density of less than 80% confluency for use in culture. Preferably, the host cells grow in a standard cell culture media, e.g., RPMI from Gibco, supplemented with antimicrobials, e.g., penicllin/streptomycin, and a fungistat, in a 5% $CO_2$ atmosphere at 37° C. On a laboratory scale, when a culture flask of host cells reaches maximum density, e.g., 80% to 100% confluency, the flasks are divided or "split" to reduce the cell density, e.g., to ⅙ the confluent density. Of course, the artisan will appreciate that this process will vary when scaled for commercial production of protozoal materials for vaccine or other purposes.

The culture system is conducted at temperatures appropriate for the selected host cell line. Preferably, incubation is conducted at a temperature ranging from about 25 to about 45° C., and more preferably from about 37 to about 41° C. Most preferred is 37° C.

Vaccines and Vaccination of Birds with Cultured *Eimeria* sp.

*Eimeria* species vaccine are known, although the organisms are obtained from live animal or egg sources. Details are given, e.g., by McDonald et al., U.S. Pat. No. 5,055,292, incorporated by reference herein in its entirety.

Purification of the merozoites obtained by the culture system is accomplished by any art-known method. Simply by way of example, and without limitation, oocysts can be released into the culture medium, and/or the cultured cells ruptured by art-known methods to harvest meroizoites. The cell debris can be removed, e.g., as described in J. A. Olson, 1990, *Antimicrob. Agents Chemother*. 34: 1435-1439. In brief, Olson's method included collecting the culture medium containing the released merozoites is collected and spun at 450×g for 10 minutes to concentrate the merozoites. The pellet containing the merozoites and the host cell debris is suspended in 0.1 M NaCl-0.05 M KCl-20% bovine serum albumin and applied to a DE-52 anion exchange column equilibrated in 75 mM Tris-40 mM $NaH_2PO_4$ -86 mM NaCl-100 mM glucose at pH 8.2. Merozoites flow through the column. Merozoites collected from the column can be tested for purity by electron microscopy as described in A. Kilejian, *J. Biol. Chem*. 249: 4650-4655, (1974).

The sporozoites or merozoites, or mixture thereof, when employed as a vaccine for avians, are preferably administrated in ovo or by injection to chicks in any physiologically-suitable medium. Preferably, they are suspended in physiologically-balanced saline, such as phosphate-buffered saline. The selected medium may optionally include one or more suspending agents, including physiologically-suitable gels, gelatins, hydrosols, cellulose, or polysaccharide gums.

In one preferred embodiment, such viable organisms, e.g., including merozoites and/or sporozoites, are preferably administered in ovo or to chicks by injection or inoculation by the following routes: parenteral, subcutaneous, scarification, and/on intramuscular administration in any suitable, art-known formulation, e.g., a compatible buffer and/or a physiologically acceptable saline, in optional combination with adjuvants and/or immune enhancers or stimulants (co-administered or administered in series, e.g., before or after vaccination).

Suitable immune stimulants include, but are not limited to, cytokines, growth factors, chemokines, supernatants from cell cultures of lymphocytes, monocytes, cells from lymphoid organs, cell preparations or cell extracts (e.g. *Staphylococcus aureus* or lipopolysaccharide preparations), mitogens, or adjuvants including low molecular weight pharmaceuticals. An immune stimulant can be administered in ovo at any time during incubation. Preferably, an immune stimulant is administered in ovo in the medium containing the dose of *Eimeria* sporozoites or merozoites, or mixture thereof.

For orally-administered vaccines/vaccination methods, any of the physiologically-suitable buffers or suspending agents that are known to the art are readily employed. In addition, the composition can be incorporated, e.g., admixed into drinking water or sprayed onto food pellets, dusted or sprayed onto corn or other grains, and the like.

For vaccination purposes, an administered dose or inoculum includes living and active cells of merozoites, oocysts, and/or combinations thereof, of two or more species of *Eimeria*.

For vaccination, a preferred dose of *Eimeria* sp. cells cultured by the inventive methods, ranges from about 10 to about $10^6$ oocysts or merozoites, or a mixture thereof, wherein the total number of oocysts and merozoites ranges from about 10 to $10^5$. The administered cells are optionally attenuated by passage through appropriate host cells, by irradiation, by recombinant mutation and/or by other art-known methods.

A more preferred dose ranges from about $10^2$ to about $10^5$ oocysts or merozoites, or a mixture thereof wherein the total number of oocysts and merozoites ranges from about $10^3$ to $10^5$.

A further preferred dose ranges from about $10^2$ to $10^5$ oocysts or merozoites, or a mixture thereof wherein the total number of said oocysts and merozoites ranges from $10^2$ to $10^5$.

Any bird, including domesticated birds in need of vaccination, is contemplated to receive this treatment. Preferably, birds receiving such vaccination are birds associated with commercial or noncommercial aviculture, e.g., birds raised in large numbers, under conditions where *Coccidial* infection is possible and undesirable. These include e.g., *Anatidae*, such as swans, geese, and ducks, *Columbidae*, e.g., doves and pigeons, such as domestic pigeons, *Phasianidae*, e.g., partridge, grouse and turkeys, *Thesienidae*, e.g., domestic chickens, *Psittacines*, e.g., parakeets, macaws, and parrots, e.g., raised for the pet or collector market. Game birds, and ratites are also contemplated to be vaccinated with the protozoa cells or other derivatives produced by the inventive culture methods. The preferred recipients of *Eimeria* sp. organisms administered for vaccination are chickens.

Any art-known route of administration or vaccination is readily employed. Thus, a dose is optionally administered in ovo to chick eggs. A dose is also optionally administered by contacting the feathers of a young, e.g., day-old chick with the vaccine organisms, or administered orally in feed and/or by spray or dropper. Oral delivery is achieved by applying a dose directly in the mouth, into the drinking water, and/or spraying the dose onto the feathers, providing oral delivery via preening. A dose is also optionally administered orally by applying or mixing the organism to pellets or gels to be ingested by the chicks.

A preferred dose to be administered in ovo to chicken eggs or day old chicks comprises oocysts or merozoites, or a mixture thereof, of two or more species of *Eimeria* selected from the group consisting of *E. tenella, E. acervulina, E. maxima, E. necatrix, E. miis, E. praecox,* and *E. brunetti*.

A preferred dose to be administered in ovo to turkey eggs or day old chicks comprises oocysts or merozoites, or a mixture thereof of two or more species of *Eimeria* selected from the group consisting of *E. meleagrimitis, E. adenoeides, E. gallopavonis, E. dispersa, E. meleagridis, E. innocua,* and *E. subrotunda*. The dose preferably includes from 10 to $10^6$ oocysts or merozoites, or a mixture thereof, for each species that is included in the dose.

Optionally, the vaccine is co-administered, e.g., simultaneously, before and/or after vaccination with *Eimeria* sp. produced by the inventive culture system, with any suitable art-known anti-*Coccidial* chemotherapeutic or chemoprophylactic agent at a dose range effective to blunt the effects of the vaccination, without impairing formation of a protective immune response in vaccinated animals. Chemotherapeutic agents include, without limitation, any effective anti-protozoal agents, e.g., antiprotozoal compounds such as antimicrobials, antibiotics, compositions that include anti-*Coccidial* antibodies, e.g., monoclonal antibodies, and/or fragments or recombinant derivatives thereof.

Combination treatments according to the invention also include, administering and/or co-administering any art-known immune stimulant along with the vaccination and/or at any other time.

A preferred method of administering the immune stimulant is simultaneously with the in ovo administration of a dose of oocysts or merozoites, or mixture of said oocysts and merozoites, during the final quarter of incubation or to day old chicks.

Another aspect of the invention is the preservation of the oocysts or merozoites, or mixture of said oocysts and merozoites, by chilling, freezing, or freeze drying. For example, when freezing the viable organisms produced by the inventive culture methods and culture system, art-known cryopreservatives are optionally employed. These include, simply by way of example, osmotic protectors such as glycerol, dimethylsulfoxide (DMSO), sugars, e.g., glucose, galactose, raffinose), proteins, e.g., serum, and/or albumin and other serum components, urea, or amino acid compositions, e.g., caseine hydrolysates, such as N-Z-AMINE® A (IPL:5X59027 from Quest International, Hoffman Estates, Ill.).

Screening for Anti-Protozoal Agents

The inventive culture system also provide an efficient and useful method for screening and identifying anti-protozoal agents, and particularly anti-*Eimeria* sp agents. Agents to be screened include potential prophylactic or therapeutic pharmaceutical agents, e.g., drugs or antibodies, among others.

In brief a species of *Sporozoea* is cultured and the culture divided. To test for prophylaxis the test agent is introduced in the culture media prior to excystation of the oocysts by the monolayer cells . To test for therapeutic efficacy the first division is grown in the culture system on normal maintenance media. In both methods, the second division is grown in the culture system on maintenance media supplemented with an agent of interest (present in solution or impregnated into test strips or test disks) to be evaluated for its ability to kill or suppress the asexually reproducing protozoal stages.

Drug sensitive protozoa or organisms with known drug resistance traits are optionally employed in order to screen for alternative treatment agents.

In an alternative strategy, a species of *Sporozoea* is cultured and the culture divided. The first division is grown in the culture system on normal maintenance media. The second division is grown in the culture system on maintenance media supplemented with an agent of interest (present in solution or impregnated into test strips or test disks) to be evaluated for its ability to kill or suppress the asexually reproducing protozoal stages. Drug sensitive protozoa or organisms with known drug resistance traits are also contemplated to be employed in the culture system in order to screen for alternative therapeutic drugs.

Development of Attenuated *Eimeria* Strains for Use In Vaccine

A well-known method to attenuate viruses for the preparation of vaccines is to pass in tissue culture to high passage levels. Through long-term culture, organisms tend to accumulate traits that are adaptive to the culture conditions and may lose virulence traits. The culture system described herein is used for the long-term propagation of *Eimeria* for the purposes of developing non-virulent strains to be used as live vaccines. The technique employs the passage of merozoite cultures as described in Example 2 for 50 or more passages.

Alternatively, merozoites that have been adapted to growth in bovine monocytes could be selected for their ability to grow on alternative cell lines such as kidney cells from a variety of species (e.g. dog, cat, cattle, or others). At various passage levels, the merozoites or oocyts derived from these continuous cultures could be tested for virulence by inoculation into day-old chicks or embryonated eggs as described in Example 4. High passage strains which have retained their ability to replicate in culture, but show reduced virulence in the host would be selected for vaccine development.

EXAMPLES

The following specific examples are included for purposes of illustration and are not intended to limit the scope of the invention unless otherwise indicated.

Example 1

Preparing a Continuous Culture System for Inoculation

A continuous culture system was prepared, as follows.

An immortalized line of bovine monocyte host cells was passaged 76 times and was found free of mycoplasma. The bovine monocyte cell line was a derivative of the cells according to Speer et al., id, supra.

The host cells were maintained in RPMI 1640 (Gibco) supplemented with penicillin (100 Units/ml), streptomycin (100 μg/ml), amphotericin (2.5 ug/ml), beta-mercaptoethanol (0.055 mM) and 10% horse or bovine serum (maintenance media).

The host cells were seeded in a 150 cm² tissue culture flask at approximately 6×10⁴ cells/ml and 15 ml per flask, resulting in a monolayer with a density no greater than 80% to 100% confluency. Cells were incubated as stationary flasks at 37° C. in a 5% $CO_2$ incubator. Cells were fed with 15 mL fresh maintenance media every 3 days and split every 7 days. Cultures were split by disrupting the monolayer with 0.25% trypsin and planting ⅙$^{th}$ of the culture into each new 150 cm² flask using the same media and incubation conditions.

Example 2

Culturing *Eimeria* Species Protozoa

A sample of *Eimeria acervulina* oocysts from infected chicken feces was prepared for culturing as follows. A slurry of feces was made by adding 10 parts of water to 1 part of feces and the oocysts were purified by sugar flotation procedure (similar to Sheather's Sugar Flotation as described in L R Ash and T C Orihel, *Parasites: A Guide to Laboratory Procedures and Identification*, ASCP Press ©1991, pp. 34-35, which reference is incorporated herein in its entirety. Oocysts were concentrated by centrifugation and resuspended in 2.5% potassium dichromate and aerated for 24 to 72 hours at room temperature to facilitate sporulation. The sporocysts were stored at 4° C. until used. The sporulated oocysts were suspended for one minute at about 25° C. in a chlorohexidine gluconate solution [Perioguard™] to kill contaminating bacteria. The chlorohexidine gluconate was removed by washing. Washing was done by pelleting the oocysts by centrifugation (800×g for 6 minutes), discarding the supernatant, (if the supernate is discarded one suspends the pellet) and then suspending pellet in 100 volumes of antibiotic/fungistatic maintenance media described by Example 1. The centrifugation and resuspension was repeated two more times.

The flasks of bovine monocytes prepared in Example 1 were used immediately after trypsinization seeding, at no more than 80% confluence. Each freshly prepared flask was then inoculated with about 1000 oocysts in 15 mL of maintenance media, prepared as described above, at a density of sporocysts/oocysts to host cells of $10^{-3}$ parasites per host cell. Cultures were incubated in stationary flasks at approximately 37° C. in a 5% $CO_2$ incubator.

The oocysts were incubated with bovine monocyte cells for 10 days, with fresh media (15 ml) added every 3 days. After 10 days, the culture supernatant and infected cells were harvested by scraping the monolayer into the culture fluid and ¹⁄₂₀$^{th}$ of the culture was inoculated onto a monolayer of fresh (uninfected) bovine monocytes at less than 80% confluency as described in Example 1. The culture was observed daily for schizonts and sporocysts/oocysts were observed to be released from the host cells and floated in the medium. The viable sporocysts/oocysts were collected by decanting the supernatant culture fluids followed by centrifugation at 800×g for 6 minutes to concentrate the parasites. The sporocysts/oocysts were used immediately or stored in culture media at 2-7° C. until used for further experiments. The cells infected with merizoites were passed for a total of 180 days and maintained their ability to continually replicate in this culture.

Example 3

Storing Sporocysy-forming Organisms

The invention also provides a method for evaluating the viability of stored *Eimeria* oocysts/sporocysts by observing infectivity in in vitro cultures and without the need for inoculation of birds.

Oocysts/sporocysts of *E. acervulina* were obtained from chicken feces by sucrose flotation using methods or could be derived from cultures as described in Example 2.

The oocysts/sporocysts were divided into five equal aliquots. Four of the aliquots were frozen at −20° C. using cryopreserving agents (such as Freezing Media™, Gibco) and the fifth aliquot stored at 2-7° C.

Viability of the four frozen samples derived from the culture were compared to the viability of the fifth sample that had been refrigerated by comparison of infectivity in bovine monocytes.

The viability comparison was conducted as follows.

Briefly, bovine monocytes were planted into 24-well plates containing sterile coverslips at a density of approximately 1-2×10⁵ cells per well, immediately prior to parasite inoculation (less than 80% confluency when inoculated) using the methods of Example 1. Serial dilutions of test samples (10−1 to 10⁻⁴ for example) were made in maintenance media (from Example 1) and 0.1 ml inoculated into duplicate wells of the 24-well plates. Plates were incubated at approximately 37° C., 3-5% $CO_2$ for 1 to 4 days. Wells were examined for the presence of *E. acervulina* infective stages by microscopic examination. Alternatively, coverslips were removed from the wells and stained with Giemsa to facilitate observation of *E. acervulina* parasites. The titer of each sample was calculated as the highest dilution showing 50% infectivity. Samples were compared for viability based on relative infectivity titer.

Example 4

Harvesting Merozoites from Culture

Merozoites were harvested when the cultures (see Examples 1 and 2) were actively replicating, generally e.g., within 10 days of the last split (subculture). Infected cells and culture supernatant were harvested using a cell scraper. Host cells were lysed by mechanical means (aspiration through a 27 gauge needle on a syringe). The merozoites were then concentrated by centrifugation (450×g for 10 minutes) and resuspended in maintenance media. The resulting suspension was then used to vaccinate test animals.

Example 5

Harvesting Oocysts from Culture

Oocysts were harvested from cultures (see Examples 1 and 2) allowed to run at 18 days or longer without a split in order to accumulate more oocysts. The culture supernatant was collected and the oocysts were purified from the cell debris using Sheather's flotation method, discussed Supra. The oocysts were then concentrated by centrifugation (405×g for 10 minutes). The pelleted oocysts were resuspended in maintenance media and used immediately.

Example 6

Vaccination of Chicks

This example demonstrates the potential for using *Eimeria acervulina* and *Eimeria tenella* oocysts and merizoites grown with the culture methods of Example 2, supra as a protective vaccine.

Experiment A: Vaccinating Chicks with *E. acervulina* and *E. tenella* oocysts

Methods

*E. tenella* and *E. acervulina* oocysts derived from cultured bovine monocytes were harvested by decanting the culture supernatant from 19 day-old cultures. The oocysts were concentrated by centrifugation and resuspended in culture media at a concentration of 100,000 oocysts per ml and used immediately.

This test employed three groups of Rhode Island Red day-old chicks. Experimental Group 1 were chicks that received tissue culture-derived oocysts for *E. acervulina* (n=3); Experimental Group 2 were chicks that received tissue culture-derived oocysts for *E. tenella* (n=3); and Experimental Group 3 were control chicks. No oocysts (n=2). Oocysts were orally administered by gavage (100 to 1000 to each chick) of Groups 1 and 2, respectively.

Results

Oocysts were observed in the feces of the Group 1 chicks after 9 days and in the feces of both the Group 1 and Group 2 chicks after 12 days. These data confirm that the culture-derived oocysts were viable and replicated in the host with the normal prepatent times expected for these species.

The Group 3 control chicks that were not given oocysts did not shed oocysts in their feces. These data confirm that there was no evidence of environmental contamination with *Eimeria* in the test birds or housing conditions. Therefore, the shedding of oocysts in Groups 1 and 2 can be attributed to the culture inoculum.

Histopathology

One chick given the *E. tenella* oocysts died from severe diarrhea.

Microscopic inspection of gut tissue sections from the chick that died confirmed a diagnosis of coccidiosis. These data indicate that oocysts derived from bovine monocyte cultures can maintain their virulence for the avian host.

Experiment B: Challenge in Chicks with *E. acervulina* and *E. tenella*

Culture and Passage of Organisms

In a preparative experiment, aliquots of oocysts from the lot of oocysts used in Part A, above, were cultured as described in Example 2, supra to produce a continuous culture of merozoites. An inoculumn of 100 oocysts in one 150 cm$^2$ flask containing bovine monocyte cells was used. The culture was passed as described in the Example 2 for two passages to ensure that no unexcysted oocysts were present in the culture.

Vaccination

One-day old chicks (one half Rhode Island Red or Barred Rock and Americana) were inoculated with cultured merozoites by oral inoculation. Birds that received the 100,000 culture-derived *E. acervulina* or *E. tenella* merozoites, prepared above, exhibited diarrhea, while day-old chicks that received a dose of 1000, 5000, and 10,000 merozoites did not exhibit diarrhea.

Fourteen days after inoculation with cultured merozoites, the chicks that were given 1000, 5000, and 10,000 merozoites and 1 uninoculated control chick were moved into an environment previously occupied by chicks that shed oocysts from Part A supra. The day-old chick that did not receive merozoites died from coccidial infection when placed in this contaminated environment. However, the chicks that had been previously inoculated with low levels of merozoites remained clinically healthy. These data indicate that the subclinical dose of merozoites was capable of inducing immunity in the birds that protected them from subsequent challenge with a lethal dose of *Eimeria*.

TABLE 1

Results of Chick Inoculation Experiments

| Birds | Exp # | # E. acervulina merozoite | # E. tenella merozoite | Fecal/Clinical Response to Merozoites | Clinical Response to Challenge |
| --- | --- | --- | --- | --- | --- |
| 2 | B | 60 | 60 | fecal negative | Not Done |
| 2 | B | 100,000 | 100,000 | Diarrhea | Not Done |
| 2 | B | 10,000 | 10,000 | fecal negative | No Clinical Signs |
| 2 | B | 5,000 | 5,000 | fecal negative | No Clinical Signs |
| 2 | B | 1,000 | 1,000 | fecal negative | No Clinical Signs |
| 1 | B | 0 | 0 | fecal negative | Died of Coccidia |

Experiment C: Inoculation of 10 Day Embryos with *E. acervulina* and *E. tenella*

In ovo inoculation by the allantoic route of 1000 bovine monocyte culture-derived merozoites (as per Example 2) of *E. acervulina* and *E. tenella* into 10 day old embryonated chicken eggs resulted in embryo death in either species of merozoites. There was no evidence of oocyst formation in the tissues. These data indicate that both species of *Eimeria* retained virulence for embryos after culture in bovine monocytes.

Example 7

Screening Anti-Protozoal Agents

The effectiveness of a proposed anti-protozoal agent against a *Sporozoea* species is evaluated by using the system of Examples 1 and 2.

A. Screening for Diclazuril 24-well tissue culture plates containing Thermonax™ (Nalge Nunc International, Naperville, Ill.) were employed, bovine monocyte cells were seeded and grown to <80% confluence in maintenance media using the methods of Example 1. Subsequently, each well was inoculated with a *E. acerulina* and *E. tenella*. The anticoccidial agent diclazuril was introduced into the media of each of 10 test wells, while 10 other wells are kept as controls. The presence of schizogony at 24, 48, and 72 hours in culture was compared between control wells and treated wells, to evaluate the anti-protozoal activity of the tested agent. Observation for parasite growth was by microscopic examination and coverslips that were stained with Giemsa. The presence of schizogony as well as the per cent reduction from the control well was used to evaluate drug treatment.

B. Screening for Other Agents 24-well tissue culture plates are employed, host cells are grown to <80% confluence in suitable maintenance media, at a temperature, and under an atmosphere appropriate for the host cells, and then each well is inoculated with a *Sporozoea* species of interest. An agent or agents to be tested is introduced into the media of each of 10 test wells, while 10 other wells are kept as controls. Growth after about 1-10 days in culture is compared between control wells and treated wells, to evaluate the anti-protozoal activity of the tested agent(s).

Observation for parasite growth can be by microscopic examination or the use of coverslips that are stained with Giemsa or a suitable stain to observe the parasites.

Example 8

Evaluating Methods for Controlling Protozoa

One way to reduce protozoal infections of domestic animals is to implement a management practice designed to remove materials that may transmit such organisms as *Coccidia* to animals housed in that location.

Such management practices are readily evaluated using the culture system and the methods of Examples 1 and 2, respectively.

Standardized samples (e.g. samples of litter) are taken from the area of interest, and processed to isolate oocysts that may be present. These are inoculated into the culture system as described by Example 2, and growth after 5-10 days is measured and correlated with samples having a known number of organisms to determine the level of growth associated with range of starting samples.

The new management practice is then implemented, and thereafter, standardized samples are collected, at locations and in quantities as taken before the change in management practice. The new samples are then cultured, and the growth at 5-10 days compared to the growth in the pre-management samples to determine any lessening of viable protozoa in the environmental area of interest.

What is claimed:

1. An anti-protozoal vaccine composition comprising a viable protozoan produced by the method of
   (a) providing a cell culture system comprising an immortalized mammalian phagocytic host cell suitable for growing *Sporozoea* species; and (b) contacting the host cell with an infectious stage of an obligate intracellular protozoan of class *Sporozoea* resulting in the growth of a merozoite population that is capable of continuous growth in the asexual phase in the host cell; wherein said contacting is performed under conditions effective for infection of the host cells; and (c) propagating the merozoite population in its asexually-dividing form;

wherein the obligate intracellular protozoan is a species that belongs to a genus selected from the group consisting of *Isospora, Cystoisospora, Cryptosporidium, Eimeria*, and combinations thereof; and wherein when the obligate intracellular protozoan is a species that belongs to the genus *Eimeria*, the *Eimeria* species is one that can infect an avian host.

2. The vaccine of claim 1 wherein the cell culture system comprises a growth media suitable for maintaining the host cell and the *Sporozoea* species organism.

3. The vaccine of claim 2 wherein the growth media comprises a reducing agent.

4. The vaccine of claim 3 wherein the reducing agent is present in a concentration effective to maintain the *Sporozoea* species organism in indefinite culture in a life cycle stage where reproduction is asexual.

5. The vaccine of claim 3 wherein the reducing agent is selected from the group consisting of β-mercaptoethanol, mercaptoethylamine, 2,3-dimercaptosuccinic acid, penicillamine, β-lactams, N-acetylcysteine, ascorbate, glutathione, and combinations thereof.

6. The vaccine of claim 5 wherein the reducing agent is β-mercaptoethanol in a concentration ranging from about 0.01 to about 0.5 mM.

7. The vaccine of claim 1 wherein the host cell is an immortalized cell retaining phagocytic activity that is derived from a mammalian reticularoendothelial cell.

8. The vaccine of claim 7 wherein the reticuloendothelial cell is a monocyte.

9. The vaccine of claim 1 wherein the method further comprising the step of splitting the culture to ensure a continuous production of merozoites.

10. The vaccine of claim 1 wherein the protozoan is an *Eimeria* species that can infect an avian host selected from the group consisting of *Eimeria tenella, Eimeria acervulina, Eimeria maxima, Eimeria necatrix, Eimeria mitis, Eimeria praecox*, and *Eimeria brunetti, Eimeria meleagrimitis, Eimeria adenoeides, Eimeria gallopavonis, Eimeria dispersa, Eimeria meleagridis, Eimeria innocua, Eimeria subrotunda*, and combinations thereof.

11. The vaccine of claim 10 wherein the protozoan is *Eimeria acervulina* or *Eimeria tenella*.

12. The vaccine composition of claim 1 comprising a pharmaceutically-acceptable adjuvant.

13. A vaccine composition comprising a food composition admixed with the vaccine composition of claim 1.

14. The vaccine of claim 1, wherein the mammalian phagocytic host cell is a monocyte.

15. The vaccine of claim 14, wherein the monocyte is a bovine monocyte.

16. A method of vaccinating an avian to elicit protective anti-protozoal immunity comprising administering the vaccine of claim 1 to an avian in need thereof, wherein the number of viable organisms is effective to elicit protective immunity in the avian.

17. The method of claim 16 wherein the avian is a domesticated bird and the protozoan is a *Coccidia*.

18. The method of claim 16 wherein the avian is selected from the group consisting of *Anatida, Columbidae, Phasianida, Thesienidae, Psittacine,* and species thereof.

19. The method of claim 16 wherein the avian is a turkey or chicken.

20. The method of claim 16 wherein the number of viable organisms comprises merozoites or oocysts, or a mixture thereof wherein the total number of said viable organisms ranges from 10 to $10^6$.

21. The method of claim 16 wherein the number of viable organisms comprises $10^2$ to $10^5$ merozoites or oocysts.

22. The method of claim 16 wherein the viable organisms comprise merozoites or oocysts that are administered by a method selected from the group consisting of oral administration, dusting or misting of feathers, in ovo injection and combinations thereof.

23. A method of screening for agents which destroy or inhibit the growth of protozoa of class *Sporozoea* comprising culturing a *Sporozoea* species of interest, with and without contact with an agent to be screened, and detecting inhibition of growth or viability relative to growth in the absence of the agent of interest, wherein the *Sporozoea* species is cultured by a method of a) providing a cell culture system comprising an immortalized mammalian phagocytic host cell suitable for growing *Sporozoea* species; and (b) contacting the host cell with an infectious stage of an obligate intracellular protozoan of class *Sporozoea* resulting in the growth of a merozoite population that is capable of continuous growth in the asexual phase in the host cell; wherein said contacting is performed under conditions effective for infection of the host cells; and (c) propagating the merozoite population in its asexually-dividing form;

wherein the obligate intracellular protozoan is a species that belongs to a genus selected from the group consisting of *Isospora, Cystoisospora, Cryptosporidium, Eimeria*, and combinations thereof; and wherein when the obligate intracellular protozoan is a species that belongs to the genus *Eimeria*, the *Eimeria* species is one that can infect an avian host.

* * * * *